US008945469B2

United States Patent
Tsukamoto et al.

(10) Patent No.: US 8,945,469 B2
(45) Date of Patent: Feb. 3, 2015

(54) MAGNETIC IMMUNOASSAY SYSTEM

(75) Inventors: Akira Tsukamoto, Toda (JP); Kazuo Saitoh, Kodaira (JP)

(73) Assignee: Hitachi, Ltd., Tokyo (JP)

( * ) Notice: Subject to any disclaimer, the term of this patent is extended or adjusted under 35 U.S.C. 154(b) by 1387 days.

(21) Appl. No.: 11/715,916

(22) Filed: Mar. 9, 2007

(65) Prior Publication Data
US 2007/0254375 A1 Nov. 1, 2007

Related U.S. Application Data

(62) Division of application No. 11/699,375, filed on Jan. 30, 2007, now abandoned.

(30) Foreign Application Priority Data

Mar. 9, 2006 (JP) .................................. 2006-063776

(51) Int. Cl.
G01N 33/543 (2006.01)

(52) U.S. Cl.
CPC ................................. G01N 33/54326 (2013.01)
USPC ............ 422/50; 422/64; 422/65; 422/186.01; 436/526; 324/248; 324/310; 324/247; 324/256; 324/257; 324/258

(58) Field of Classification Search
USPC ................... 422/50, 65, 64, 186.01; 436/526; 324/248, 310, 247, 256–258
See application file for complete search history.

(56) References Cited

U.S. PATENT DOCUMENTS

| | | | |
|---|---|---|---|
| 5,145,784 A * | 9/1992 | Cox et al. ....................... | 436/526 |
| 5,311,125 A * | 5/1994 | Krause et al. ................. | 324/201 |
| 6,123,902 A * | 9/2000 | Koch et al. ..................... | 422/50 |
| 6,483,303 B2 * | 11/2002 | Simmonds et al. ............ | 324/239 |
| 6,853,185 B2 * | 2/2005 | Tsukamoto et al. ........... | 324/248 |
| 2002/0135358 A1 * | 9/2002 | Sager et al. .................... | 324/204 |

* cited by examiner

Primary Examiner — Bao Thuy L Nguyen
Assistant Examiner — Pensee Do
(74) Attorney, Agent, or Firm — Mattingly & Malur, PC

(57) ABSTRACT

A magnetic immunoassay system with a mechanism for compensating the direct current residual magnetic field in the vicinity of the specimen measurement position, in a direction perpendicular to the magnetic marker direction of magnetization for the measurement target. This invention reduces the effects of the magnetic field emitted from the unbound magnetic marker due to the residual magnetic field in the specimen solution and detects with high sensitivity the signal of the bound target magnetic marker. The magnetic field at the measurement position is regulated so as to intersect the direction of magnetization of the magnetic marker for the measurement target, in order to make the magnetization direction of the magnetic marker that is unbound due to residual magnetism or remanence in the sample solution, intersect the magnetization direction of the magnetic marker for the measurement target. The signal of the bound target magnetic marker can be therefore measured with high sensitivity since it is isolated from the unbound magnetic marker signal.

8 Claims, 16 Drawing Sheets

MAGNETIC FIELD

DIRECTION OF RESIDUAL FIELD

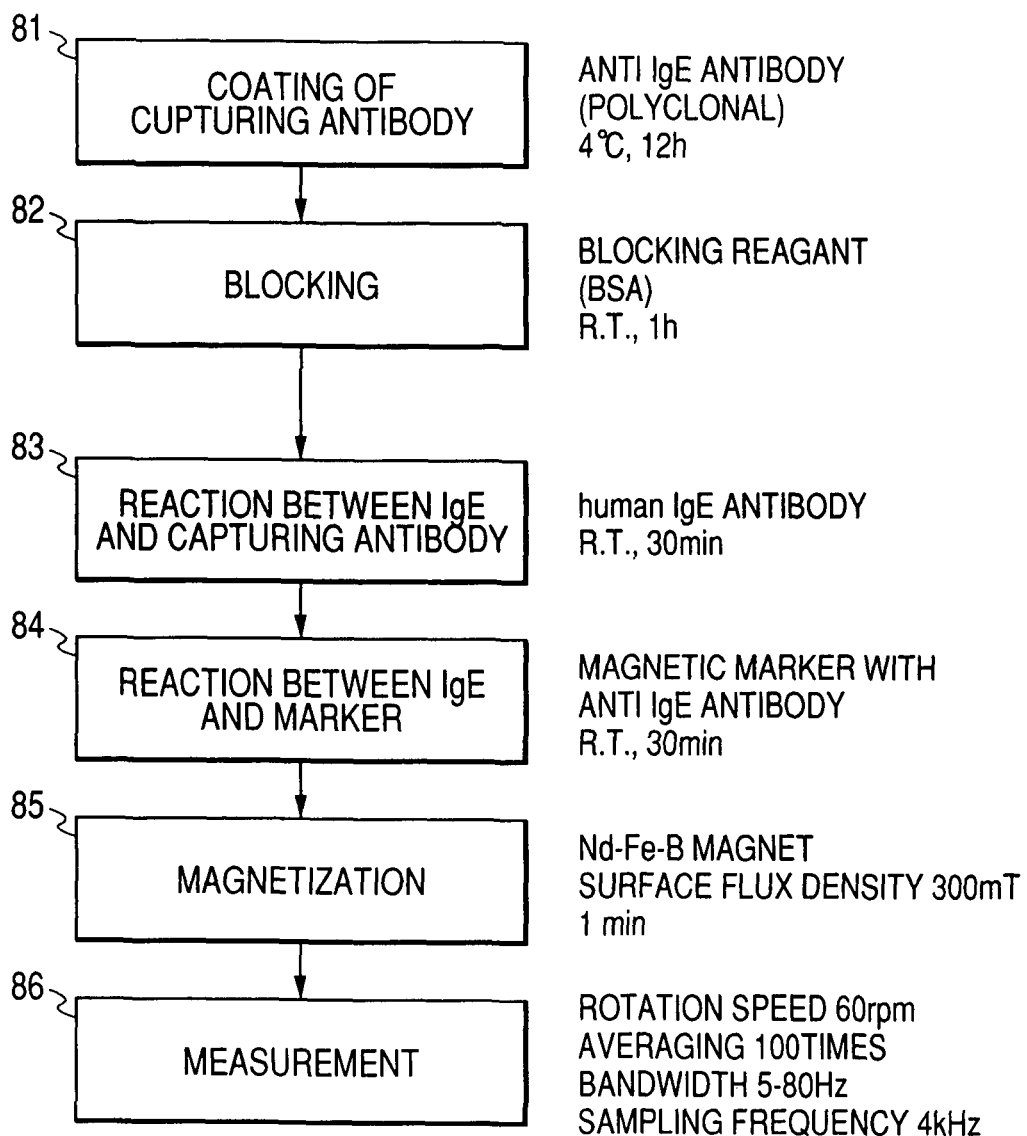

FIG. 15
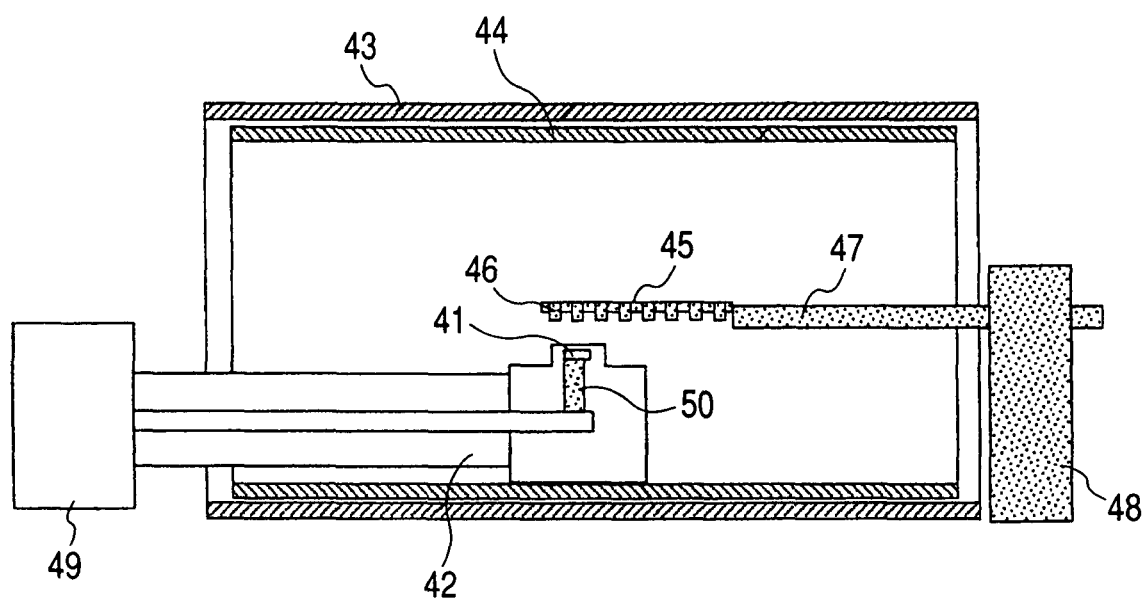
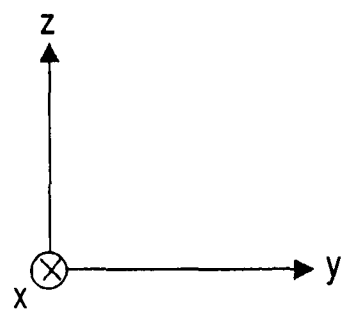

MAGNETIC IMMUNOASSAY SYSTEM

CROSS-REFERENCE TO RELATED APPLICATION

This application is a Divisional application of U.S. application Ser. No. 11/699,375 filed Jan. 30, 2007 now abandoned. Priority is claimed based on U.S. application Ser. No. 11/699,375 filed Jan. 30, 2007, which claims the priority of Japanese Patent Application No. 2006-063776 filed on Mar. 9, 2006, all of which is incorporated by reference.

FIELD OF THE INVENTION

The present invention relates to a system for analyzing different types of protein (immunoglobulin, tumor markers, and hormones, etc.), disease-causing germs, cancer cells, DNA and environmental toxins by utilizing magnetic nanoparticles, and relates in particular to a magnetic immunoassay system utilizing a superconducting quantum interference device (SQUID).

BACKGROUND OF THE INVENTION

Demands are increasing in recent years for high sensitivity in the examination of environmental toxins, DNA, cancer cells and disease-causing germs of different types by their immuno-reaction. This demand has spurred intensive development of immunoassay systems. The general method for making an immunoassay is an optical method that labels an antibody (for detection) selectively bound to an antigen for detection, by optically marking it with an optical fluorescent enzyme, detecting the reaction of the bound antibody-antigen as an optical signal from the optical marker to find the type and quantity of the antigen. However, this optical method does not have adequate detection sensitivity and requires a process for washing off the unbound optical marker (BF separation).

A magnetic method for detecting antigen-antibody reactions has been proposed in recent years that utilizes a magnetic nanoparticles and a SQUID magnetic sensor to achieve detection sensitivity surpassing the optical method. This magnetic method detects antibodies magnetically labeled with magnetic nanoparticles (hereafter called magnetic markers), by utilizing a SQUID magnetic sensor possessing extremely high sensitivity.

Methods for detecting magnetic markers are based on:
(1) measuring the susceptibility,
(2) measuring the magnetic relaxation
(3) measuring the residual magnetism (remanence).
The above methods (1) through (3) are described next.

(1) Method for Measuring the Susceptibility

In this method, a direct current magnetic field is applied to magnetize the magnetic marker from a direction intersecting the SQUID magnetic sensor flux detection direction, and measures the change in the magnetic field occurring due to magnetic marker movement within flux detection range of the magnetic sensor (for example, patent document 1). Another variation of this method applies an alternating current magnetic field to the magnetic marker, and utilizes the SQUID magnetic sensor to detect that signal as an antigen-antibody reaction (for example, patent document 2).

(2) Method for Measuring Magnetic Relaxation

In this method, the magnetic relaxation is measured up to one second immediately after a 1 mT pulse magnetic field was applied to a magnetic marker. The measurement is made in the solution where the unbound magnetic marker is present, and the bound magnetic marker is detected (for example, in non-patent document 1 and non-patent document 2). Methods that quantitatively detects the sample in the liquid phase or solid phase by measuring the magnetic relaxation, and a method that performs magnetic relaxation measurement by utilizing chemical compounds and also utilizes them for analysis and magnetography have also been reported (for example, patent document 3).

(3) Method for Measuring Remanence

Relaxation of remanence in the magnetic nanoparticles does not occur when the size of magnetic nanoparticles becomes large. This method applies a magnetic field of approximately 0.1 T to the magnetic marker at a location separated from the SQUID magnetic sensor to generate remanence in the magnetic marker. A plate holding the sample is moved to the SQUID magnetic sensor for measuring the residual magnetism (for example, patent document 4, non-patent document 4).

In typical immunoassay tests, the measurement is made after B/F (bound free) separation (washing process) to eliminate the unbound magnetic markers. However, the unbound nanomagnetic particles are capable of moving randomly in the solution due to Brownian motion so that measurement can be made without a B/F separation (for example, non-patent document 3). Eliminating the B/F separation has the advantage that the testing time is short and the system can be simplified.

A specific example relating a method for magnetically detecting the antigen-antibody interaction is described next (for example, non-patent document 4).

FIG. 1A through FIG. 1E are drawings of the procedure in a typical method for measuring the residual magnetism or remanence in a magnetic immunoassay method of the related art without a B/F separation and utilizing the antigen-antibody interaction.

In a pre-process as shown in FIG. 1A, an antibody 2, which is bound to an antigen serving as the detection target, is fixed in the bottom 1a of the sample container 1. Hereafter this is referred to as a capturing antibody. Next, a block reagent 3 is applied to prevent nonspecific adsorption onto the side walls, and this blocking reagent 3 covers the inner walls of the container. When a sample 5 containing a fixed amount of a substance for measurement is injected into the sample container 1 prepared in this way, an antigen 6 in the sample binds to the capturing antibody 2 via an antigen-antibody interaction as shown in FIG. 1B. When a solution containing a magnetic marker for binding with the antigen 6 is next injected into the sample container, a portion of the magnetic marker 7b binds by an antigen-antibody interaction to an antigen 6a linked to the capturing antibody 2 as shown in FIG. 1C. A portion of the marker 7a also binds to an antigen 6b in the solution that is not bound to the capturing antibody 2. An unbound marker 7c not bound to an antigen, and a magnetic marker 7b bound to the antigen 6b in the solution, move randomly by Brownian motion.

When an external magnetic field is applied to the sample in this state, in the direction of the large arrow shown in FIG. 1D, all of the magnetic markers are magnetized in the direction that the magnetic field is applied. The small arrows in the drawing show the direction of magnetization of each marker. When using magnetic markers containing magnetic nanoparticles that possess remanence (residual magnetism), the remanence still remains even when there is no longer a magnetic field.

However, when no magnetic field was applied as shown in FIG. 1E, the unbound magnetic marker 7c, and the magnetic marker 7b bound to the antigen 6b in the solution move randomly in the solution due to Brownian motion so that the direction of magnetization (direction of magnetic momentum) also becomes random, and the magnetic signals from these magnetic markers cancel each other out, so that normal magnetic signals cannot be generated. In other words, there is no need to eliminate the unbound magnetic markers in a washing process. Brownian motion however does not occur in the magnetic marker 7a bound to the antigen 6a bound to the capturing antibody 2 so that remanence is retained in the direction of magnetization even when no magnetic field was applied, and a magnetic signal is generated that is proportional to the amount of antigen 6a bound to the capturing antibody 2. The amount of antigen 6a bound to the capturing antibody 2 is dependent on the amount of antigen contained in the sample so that the amount of an antigen to be investigated can be measured by detecting this magnetic signal with a high-sensitivity SQUID magnetic sensor.

In view of the fact that immunoassays using optical markers require a washing process (B/F separation) process, immunoassays using magnetic markers possess a large advantage since one characteristic feature is that no washing process is required.

[Patent document 1] JP-A No. 33455/2001
[Patent document 2] JP-A No. 133458/2001
[Patent document 3] JP-A No. 513551/1998
[Patent document 4] JP-A No. 257425/2005
[Patent document 5] JP-A No. 508031/1999
[Non-patent document 1] Y. R. Chemla, et al.: Proc. National Acad. Sciences of U.S.A. 97, 14268 (2000)
[Non-patent document 2] A. Haller, et al.: IEEE Trans. Appl. Supercond. 11, 1371 (2001)
[Non-patent document 3] R. Kotitz, et al.: IEEE Trans. Appl. Supercond. 7, 3678 (1997)
[Non-patent document 4] K. Enpuku, et al.: IEEE Trans. Appl. Supercond. 13, 371 (2003)

SUMMARY OF THE INVENTION

Performing immunoassay analysis possessing the advantage that remanence or magnetic relaxation is measured without a washing (B/F separation) process, requires that the direction of magnetic monemtum of each unbound magnetic marker within the solution be random by Brownian motion. The magnetic signals from the unbound magnetic marker 7c in this case cancel each other out so that no magnetic signals are detected from the solution (FIG. 1E). However, results from experiments conducted by the present inventors revealed that unbound magnetic markers emit magnetic signals from within the solution due to the unbound magnetic markers being aligned in the direction of a residual magnetic field within the magnetic shield section. The residual (magnetic) field within the periphery of the sensor and the sample could be reduced by magnetic shielding but completely reducing this magnetic field to zero was impossible.

The state of magnetic markers in the case where a magnetic field is completely blocked and sufficient Brownian motion is occurring, and the case where a residual magnetic field is present are shown in the drawings in FIG. 2A and FIG. 2B. In the case as shown in FIG. 2A where the magnetic field is completely blocked, each nanoparticle is moving randomly due to Brownian motion so that the magnetism from each of the magnetic markers mutually cancel each other out so that no macro magnetic signal is generated. The arrow 10 shown in the vicinity of the magnetic marker 11, indicates the direction of magnetic momentum retained by the respective markers 11. However, in the residual magnetic field as shown in FIG. 2B, a bias is applied in that direction so the movement is not completely random. The strength of this magnetic alignment varies with the size of the residual magnetic field but tends to array in the direction of the residual magnetic field. Macro magnetic signals are therefore generated in the direction of that residual magnetic field. The magnetic signals from these unbound magnetic markers become background signals (noise) causing a drop in the signal-to-noise (SN) ratio and an increase in the minimum detection limit when attempting to measure a fixed magnetic marker.

Even though the residual magnetic field can be lowered to the required level by utilizing a magnetic shield with a highly sealed multi-layer structure, the magnetic shield should ideally be as simple as possible in view of the need to lower equipment costs and provide operating features such as replacement of samples, etc.

Whereupon, an object of the present invention is to provide a method capable of easily eliminating the effects of residual magnetic fields that cannot be reduced by magnetic shields, and also to provide a high-sensitivity magnetic immunoassay system capable of sufficiently reducing the effect of signals from unbound markers.

The inventors perceived that the above described problems could be resolved by making the magnetization direction of the magnetic marker bound to a capturing antibody, and the magnetization direction of an unbound magnetic marker mutually intersect each other.

The magnetic signal waveform detected in the SQUID when a magnetic sample is made to pass under a SQUID magnetometer is described while referring to FIG. 3. The coil surface of the pickup coil is arranged along a flat x-y plane, and the magnetic sample passes in the x direction directly beneath the pickup coil parallel to the x-y plane. The x-y plane view and the x-z plane view in FIG. 3 show the positional relation between the pickup coil and magnetic sample and the direction of movement of the magnetic material are shown. The same figure also shows the signal waveform, which is x position dependence due to the magnetic orientation of the magnetic sample. The (a), (b), (c) in this figure, show the case where the magnetic sample is respectively magnetized in the x direction, y direction, and z direction.

As the magnetic sample approaches the SQUID while magnetized in the x direction, the flux generated from the magnetic sample starts to bind to the pickup coil section of the squid from bottom to top so that the SQUID detects the flux, and the SQUID output signal changes. When the sample reaches the exact center of the pickup coil, the flux from the sample binds to the pickup coil from bottom to top but the SQUID output signal becomes zero since the same amount of return flux to the sample binds to the pickup coil from top to bottom at the same time. Moreover, as the sample moves farther away from the SQUID, the flux from the magnetic material binds from top to bottom to the SQUID pickup coil so that the output signal changes to the minus direction. The signal once again becomes zero as the sample moves even further away. Setting the x position above the sensor as the origin point, makes the waveform symmetrical around the origin point. The polarity of the magnetic signal varies according to the magnetic polarity and the polarity of the SQUID pickup coil so that the upward and downward directions of the waveform that is obtained might sometimes be reversed.

Next, when the magnetic sample is approaching the SQUID while the magnetic sample is magnetized in the y direction, the flux generated from the magnetic sample that entered the SQUID from one side, come out from the other side of the SQUID. In this case there is no regular magnetic signal bound to the SQUID, and the output signal is always zero.

Next, when the magnetic sample is approaching the SQUID while the magnetic sample is magnetized in the z direction, the flux generated from the magnetic sample starts to bind to the SQUID from top to bottom so that the SQUID detects the flux, and the SQUID output signal changes. When the sample moves to directly below the pickup coil, the flux binds to the pickup coil from bottom to top so that the SQUID output signal appears extremely large in the reverse direction. Moreover, when the sample moves away from the SQUID, the flux again binds to the SQUID from top to bottom so that an output signal is generated in the original direction.

As can readily be understood from viewing the magnetic signals for cases (a), (b), (c), the magnetic signal is symmetrical around the origin point utilizing the pickup coil centerpoint serving as the boundary in the (a) case. Therefore, after the signal was obtained, it (the signal) is divided up in the x direction and if the difference between each signal is found, then a signal can be obtained that is twice the amplitude of a signal on one side of the origin point. In the (c) case however, the signal varies symmetrically on an origin point along the vertical axis so that processing it in the same way yields a signal of zero. If the processing uses the sum of the signals, then the signal will have twice the amplitude in the (c) case, versus a signal of zero in the (a) case.

The desired signal can therefore be obtained by processing by adding or subtracting according to the magnetization direction of the signal to be measured.

Therefore if the captured magnetic marker to be measured is magnetized in the x or the z direction, and the magnetization direction of the unbound magnetic marker in the solution causing the noise is controlled to intersect the magnetization direction of the bound magnetic marker, then the waveforms that are obtained will be two waveforms with different symmetry, or in other words, the sum of the captured marker waveform and the waveform of the marker within the solution. The waveform of the captured marker can be easily obtained by utilizing the difference in symmetry between these measured waveforms.

The magnetic orientation of the magnetic marker in the solution can be controlled so as to intersect the magnetic direction of the bound magnetic marker, by setting the residual magnetic field component along the magnetic moment of the bound magnetic marker to zero. Another method is to apply a magnetic field in a direction intersecting the magnetic direction of the marker, to control the magnetic direction of the unbound magnetic marker within the solution so as to intersect the magnetic direction of the fixed magnetic marker. As can be seen from the example shown in FIG. 3, if the magnetic direction of the unbound magnetic marker within the solution is controlled in the y direction, then there is no need to isolate the (magnetic) signals since the SQUID cannot detect magnetic signals from a magnetic marker magnetized in the y direction. Yet another method is to align the magnetic direction of the unbound marker within the solution to intersect the magnetic direction of the fixed magnetic marker even when using a magnetic shield structure where the direction of the residual magnetic field within the shield intersects the direction of magnetization of the fixed magnetic marker. A combination of these methods may also be used.

In FIG. 4, a SQUID gradiometer containing a first order planar gradiometric pickup coil is utilized instead of a SQUID magnetometer. FIG. 4 shows the signal waveforms detected in the SQUID when a magnetic sample has passed over it. The x-z planar surface is omitted in FIG. 4. The coil surface of the gradiometric pickup coil is also arrayed along the x-y planar surface in FIG. 4, and the magnetic sample passes along the x direction, directly beneath the pickup coil parallel with the x-y planar surface. The direction perpendicular to the pickup coil is z, the sample direction of movement is x, and here y is a direction perpendicular to x and z. The (a), (b), and (c) in FIG. 4 show the case where are each the same as (a), (b), and (c) in FIG. 3, and the case is shown where the magnetic sample is magnetized in the x, y, and z directions. The differential direction of the gradiometric pickup coil is the x direction, and the solid line and the dotted line of the pickup coil in the drawing show that the pickup coil polarity is reversed. Unlike FIG. 3, the signal waveforms detected in the SQUID when the magnetic sample is magnetized in the x direction, y direction and the z direction are bilaterally symmetrical, zero and are central symmetrical. Just as with the magnetometer shown in FIG. 3, the signal waveforms detected in the SQUID from the sample magnetized in the z direction, and the sample magnetized in the x direction possess different symmetry so that the signals can be easily isolated. The magnetic signals from the sample magnetized in the y direction, as expected, cannot be detected so there is no need to isolate the signals.

Therefore, just as with the magnetometer, the magnetic orientation of the unbound magnetic marker in the solution can be controlled so as to intersect the magnetic direction of the bound magnetic marker, by setting the residual magnetic field component along the direction of the magnetic moment of the bound magnetic marker to zero. Another method is to apply a magnetic field in a direction perpendicular to the magnetic direction of the magnetic marker, to control the magnetic direction of the unbound magnetic marker within the solution so as to intersect the magnetic direction of the fixed magnetic marker. Yet another method is to align the magnetic direction of the unbound magnetic marker within the solution to intersect the magnetic direction of the fixed magnetic marker even when using a magnetic shield structure where the direction of the residual magnetic field within the shield intersects the direction of the fixed magnetic marker. A combination of these methods may also be used.

If a signal with a different symmetry can be obtained from the different magnetization direction of the sample, then the desired signal waveform can be obtained with the method of this invention even if utilizing a higher order gradiometer or a pickup coil with a different structure or shape.

Reducing the direct current field to zero in all directions with a magnetic shield is impossible but the magnetic field in one direction can easily be controlled, as used in this invention. A compensation coil can be installed for example in the vicinity of the SQUID magnetic sensor and the residual magnetic field components in the vicinity of the measurement position canceled in one direction out by adjusting the direct current flowing to the compensation coil. Moreover, controlling the magnetization direction of unbound magnetic markers in the solution to a direction perpendicular to the magnetization direction of bound magnetic markers is comparatively simple. A permanent magnet or a coil for example can be installed to control the magnetization direction of unbound magnetic markers in the solution by applying a magnetic field. Controlling the direction of the residual magnetic field within the shield is also comparatively simple. In the case of a cylindrical magnetic shield for example, the shield rate along the center axis of the tube is lower than a direction perpendicular to the center axis so that a magnetic field can be left remaining along the center axis in the center of the cylindrical magnetic shield.

Moreover, by combining with the above method, a direct current magnetic field left remaining in the vicinity of the sample measurement position of this invention can be controlled in a direction perpendicular to the magnetization direction of the magnetic nanoparticles in the object for measurement.

This invention is capable of easily isolating signals from bound magnetic markers even when magnetic signals are emitted from magnetic markers in a liquid state due to a residual magnetic field. The present invention can therefore eliminate the effects from magnetic signals emitted by magnetic markers in a liquid state and provide a high sensitivity immunoassay. Moreover this invention does not require a magnetic shield with good multilayer sealing that was required for high sensitivity immunoassays so this invention can reduce equipment costs and improve operability.

BRIEF DESCRIPTION OF THE DRAWINGS

FIG. 8 is a flow chart showing the test protocol used in the embodiment;

FIG. 15 is a drawing showing the structure of the immunoassay system of the third embodiment.

DETAILED DESCRIPTION OF THE PREFERRED EMBODIMENTS

First Embodiment

The following description utilizes antibodies labeled with magnetic nanoparticles (magnetic markers) containing residual magnetic signals, and the description of the embodiment of this invention utilizes a magnetic immunoassay system for detecting magnetic signals from a sample reacting with a test reagent in a first-order planar SQUID gradiometer as an example. The following disclosure is nothing more than an embodiment of this invention, and does not limit the technical scope of this invention.

Figure 5:
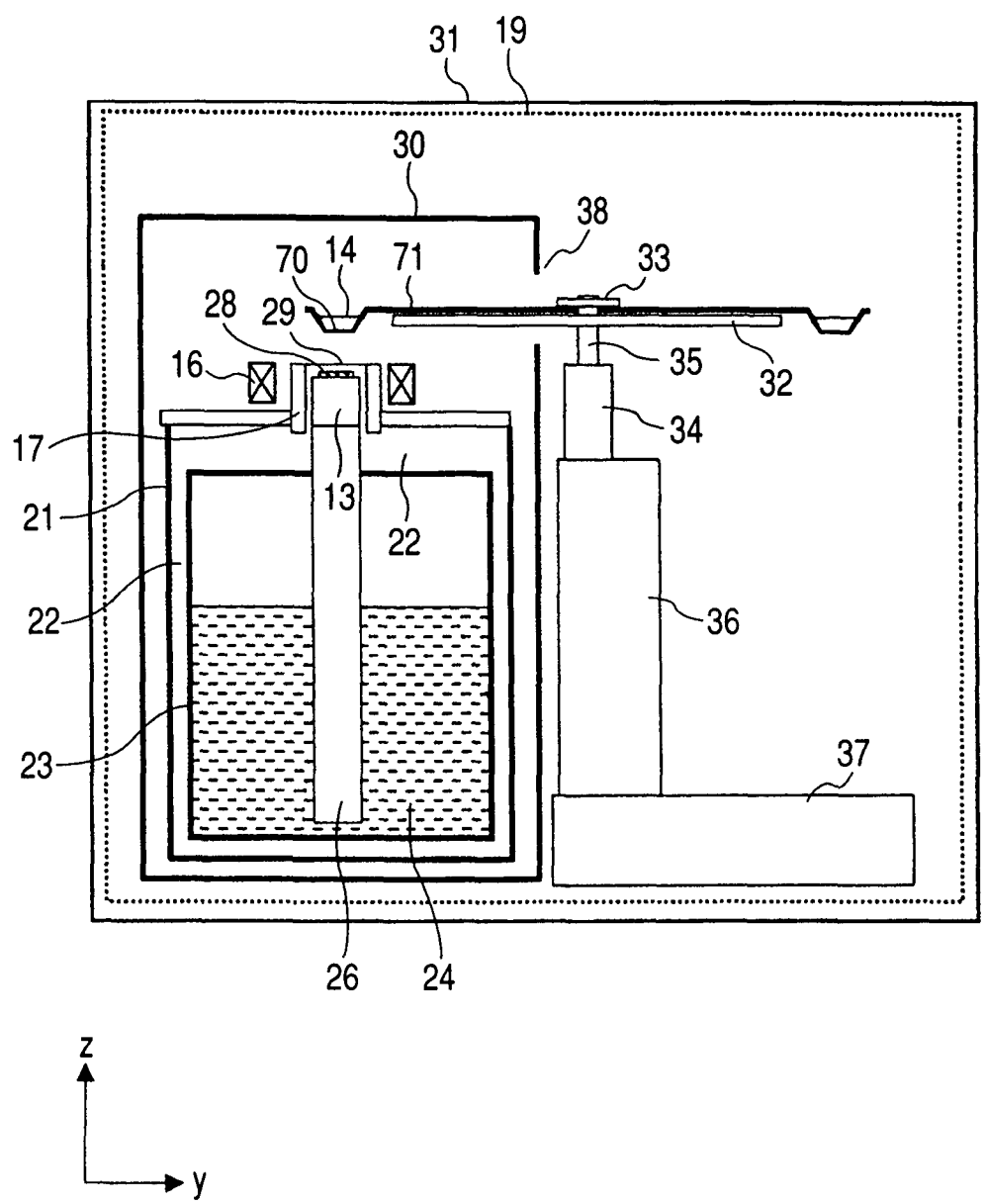
FIG. 5 is a drawing showing a typical structure of the immunoassay system including a compensation coil for the first embodiment of this invention.

FIG. 5 is a cross sectional view showing the structure of the first-order gradiometer SQUID of the first embodiment of this invention. In order to reduce the input of magnetic environmental noise into the SQUID, the cooler device (made up of an outer tank 21, a vacuum layer for thermal insulation 22 and inner tank 23) for cooling the SQUID is enclosed by an RF shield 19 and magnetic shields 30, 31. The RF shield 19 is made from metal material with low electrical resistance such as aluminum. The magnetic shields 30, 31 are made from high permeability material such as permalloy. A portion of the magnetic shield 30 is formed with a slot 38 to allow insertion of the sample container 71.

Figure 6:
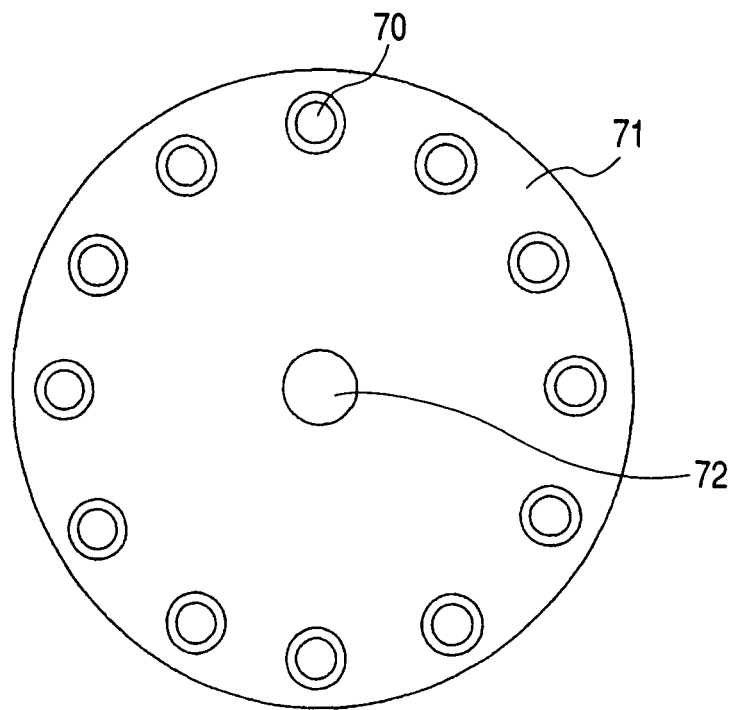
FIG. 6 is a drawing showing a sample container used in the first embodiment.

A sample container 71 in the nonmagnetic disk shaped sample stage 32 is clamped to a rotating shaft 35 by a clamping screw 33. A flat (plan) view of the sample container 71 is shown in FIG. 6. This container is made from highly nonmagnetic material such as plastic. The container 71 is formed in a circular shape and contains cone-shaped recess sections 70 at 12 points on the outer circumference. A hole 72 is drilled in the center for clamping to the equipment. The diameter of the recess sections in the bottom is 5 millimeters.

A sample 14 containing a magnetic marker is inserted in the recess section 70 in the sample container. The sample stage 32 rotated via the rotating shaft 35 connected to a rotation mechanism 34. The rotation mechanism 34 is supported to allow movement in three dimensions on the motion stages 36, 37. The movement of the motion stages 36, 37 via the rotation mechanism 35 makes a section of the sample container 71 pass through an insertion slot 31, move to the internal section of the magnetic shield 30, and adjust the position so that the bottom of the recess section 70 approaches a sapphire window 29. As described using FIG. 1, an antibody 2 bound to an antigen and serving as the object for detection, is clamped in the bottom of the recess section 70 of the sample container, and is covered on the peripheral walls by a blocking reagent 3.

The pickup coil of the SQUID 28 is installed in the lower part of the sapphire window 29 in order to shorten the distance between the sample 14 and the SQUID 28 pickup coil, and to boost the spatial resolution and detection sensitivity for magnetic signals generated by the sample. The rotation of the sample container 71 causes the multiple samples 14 to pass above the pickup coil of the SQUID 28, and the magnetic signal is measured at that time. The sapphire window 29 is clamped to the nonmagnetic cylindrical piece 17 and is capable of being positioned upward or downward. A compensation coil 16 is wound around this cylindrical piece 17 for compensating the residual magnetic field. Making an electrical current flow in this coil applies a compensating magnetic field in a direction perpendicular to the SQUID pickup coil. The center axis of the compensation coil 16 passes along the center of the SQUID pickup coil. A solenoid coil with a simple structure was utilized here, however a Helmholtz coil or other coil shapes providing a more uniform magnetic field distribution may also be utilized. In other words, the effect of this invention can be obtained if the magnetic field for the sample detection position above the SQUID can be compensated.

The SQUID 28 is installed in vacuum layer for thermal insulation 22 of the cooling container and is indirectly cooled by the liquid nitrogen 24 via a sapphire rod 13 and a copper rod 26 possessing high thermal conductivity. The outer tank 21 and an inner tank 23 in the cooling device are made non-magnetic material such as SUS and FRP (fiber reinforced plate). Interposing the sapphire rod 13 between the SQUID 28 and the copper rod 26 has the effect of reducing the effect of magnetic noise generated from the copper rod 26.

Figure 7:
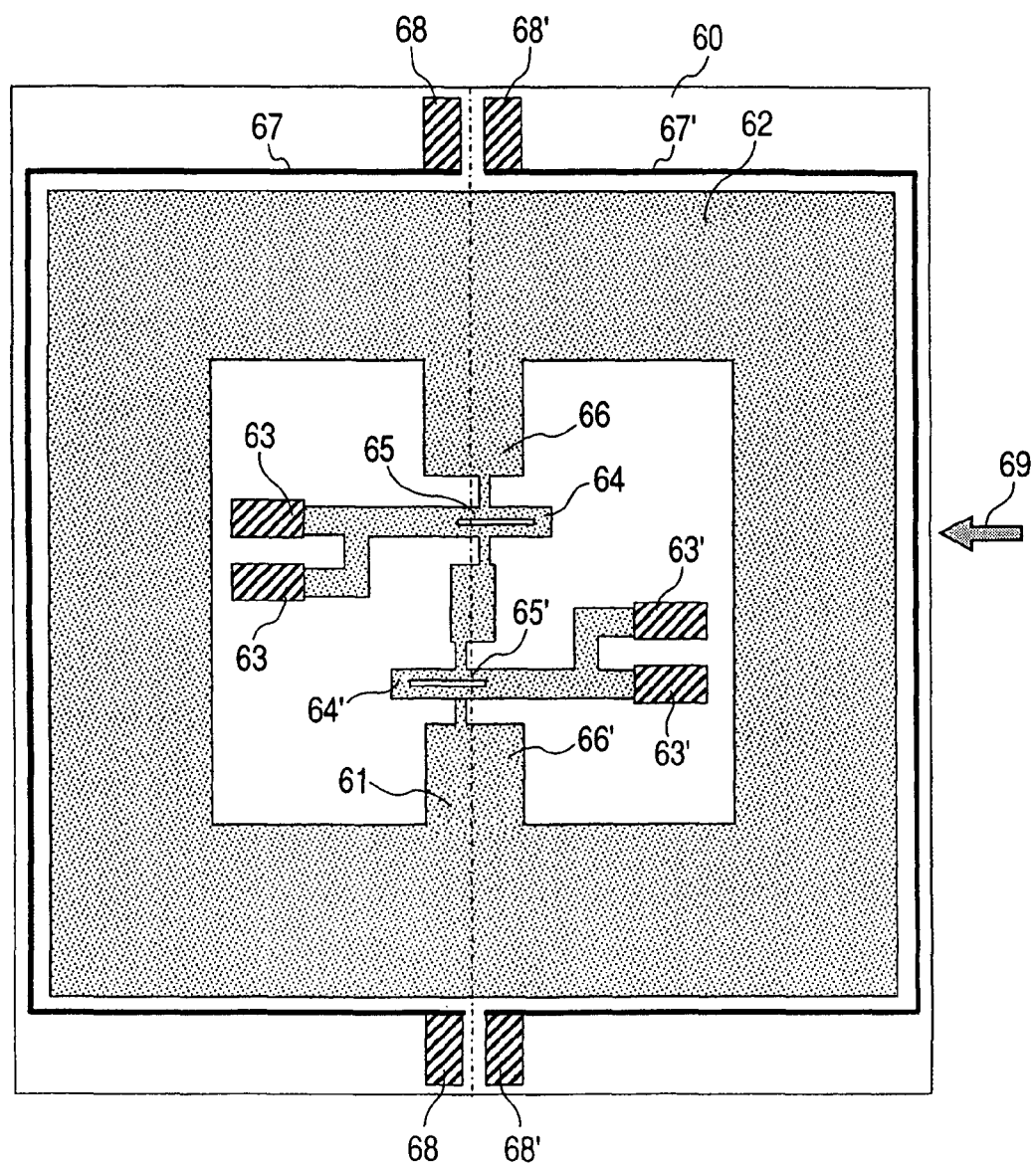
FIG. 7 is a drawing showing the high-temperature superconducting SQUID used in the embodiment of this invention.

A high-temperature superconducting SQUID gradiometer was utilized as the SQUID 28 in the immunoassay system of the first embodiment. FIG. 7 is a flat (plan) view showing the structure of the high-temperature superconducting SQUID gradiometer. The pickup coil 62 and the SQUID ring 64 were fabricated by patterning high-temperature superconductive material such as $YBa_2Cu_3O_x$ formed on a bicrystal substrate 60 of single crystal such as $SrTiO_3$ or MgO with a shifted crystal orientation and bonded to a bicrystal plane 61. The SQUID ring 64 cuts across the bicrystal plane 61 formed on the bicrystal substrate 60. A grain boundary Josephson junction 65 was formed in the superconducting thin film formed on the bicrystal plane 61, to consequently form two grain boundary Josephson junctions 65 on the SQUID ring 64. On the SQUID used here, two SQUID rings 64 and 64' coupled to the same pickup coil are formed on one substrate. Among these two SQUID rings, the ring having the better characteristics is used here.

The pickup coil 62 is made up of a gradiometric pickup coil in a figure "8" shape of two loops of 5 millimeters on one side. When magnetic flux enters the pickup coil 62 the differential between the shielding currents flowing in each loop of the two loops flows into the SQUID rings 64, 64' via the center section 66 of the pickup coil. This electrical current is detected as a flux. The feedback coils 67 and 67' are formed as circuit patterns on the substrate 60 so as to enclose one loop on the pickup coil 62. One among the two feedback coils 67, 67' were used. The gold wiring pads 63, 63' and 68, 68' were patterned on the superconducting thin film when a wiring connection was required. The wiring pad 63 was electrically connected to the SQUID ring 64, and the wiring pad 68 was electrically connected to the feedback coil 67.

Figure 4:
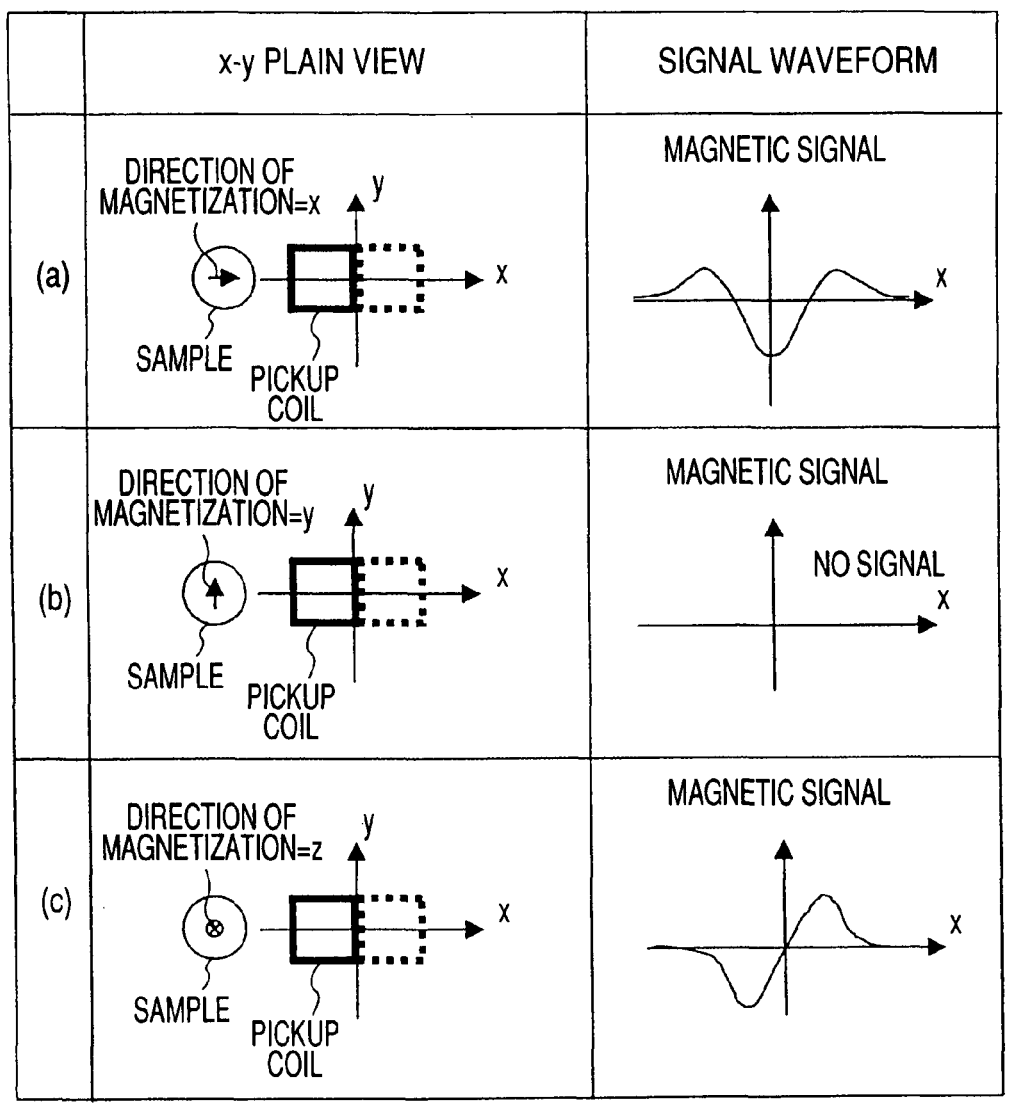
FIG. 4A, FIG. 4B and FIG. 4C are drawings showing the relation between the magnetization direction of the sample when using a first-order planar gradiometer, to the detected magnetic signal waveform.

The sample container passes above the SQUID along the arrow direction 69 in FIG. 7. The sample piece is magnetized in a direction perpendicular to the bottom of the container. This magnetizing direction is perpendicular to the pickup coil surface. The relation between the SQUID and the magnetic signal emitted from the bound magnetic marker, as well as the magnetic signal waveform that is obtained therefore correspond to those shown in FIG. 4C.

The total IgE (immunoglobulin E) was detected in the first embodiment. The test protocol is shown in FIG. 8. First of all, in step 81, a capturing antibody (anti IgE antibody) was fixed to the bottom of the recess section 70 of the non-magnetic reaction chamber 71. The capturing antibody was directly attached to the reaction chamber in the example of the first embodiment. However, the same measurement can be performed by binding the capturing antibody to a solid such as polymer beads or cellulose string having a size of several microns or larger and incapable of large movement during measurement, and placing this in the recess section 70 of the non-magnetic reaction chamber 71.

After adding the antibody, the blocking process was performed in step 82 using BSA (Bovine serum albumin). After washing, the test sample including IgE was placed in step 83, and a reaction between the capturing anti IgE antibody and IgE was made to occur. A PBS (phosphate buffered saline) solution of 50 µl containing 100 pg of IgE was used in the test sample. A PBS solution of 50 µl not containing IgE was utilized as the reference sample. After 30 minutes a magnetic marker was placed from above in step 84 and a reaction between the IgE and magnetic marker made to occur. The first embodiment utilized a magnetic marker with a structure where the anti IgE antibody was attached to the surface of polymer-coated $Fe_3O_4$ (magnetite) nanoparticles with a diameter of 25 nm. Thirty minutes later in step 85 a permanent magnet (neodymium magnet, diameter 30 mm, surface flux density 300 mT) was placed on the bottom of the reaction chamber for one minute, and magnetization in the z direction was performed as described in FIG. 4C. After magnetization, the sample container was mounted in the measurement system and the magnetic signals generated from the sample were measured in step 86. The conditions for each of these steps were recorded to the side of each step.

Figure 9A:
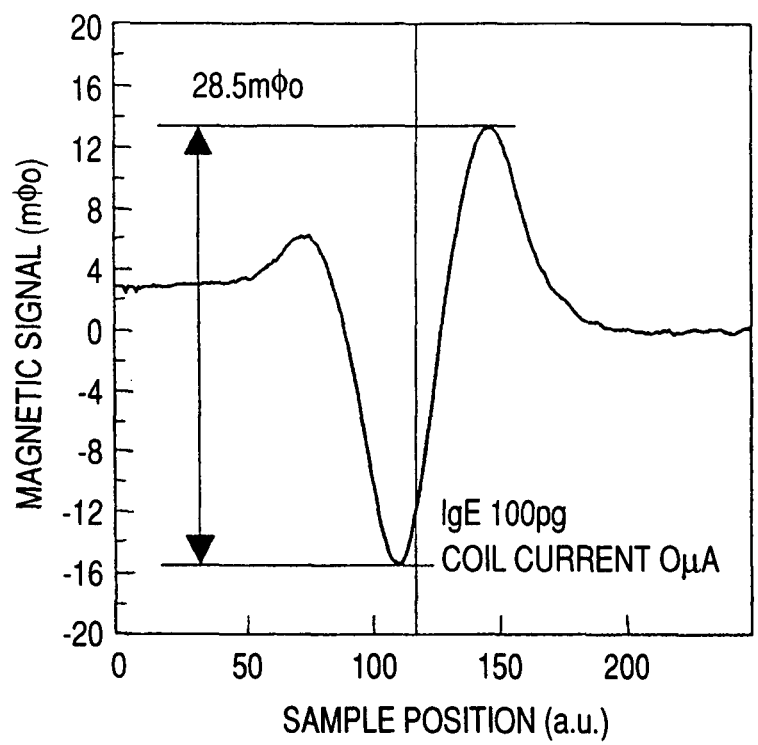
FIG. 9A is a magnetic signal waveform obtained from a sample containing 100 pg of IgE measured with no electrical current flowing in the compensation coil.
Figure 9B:
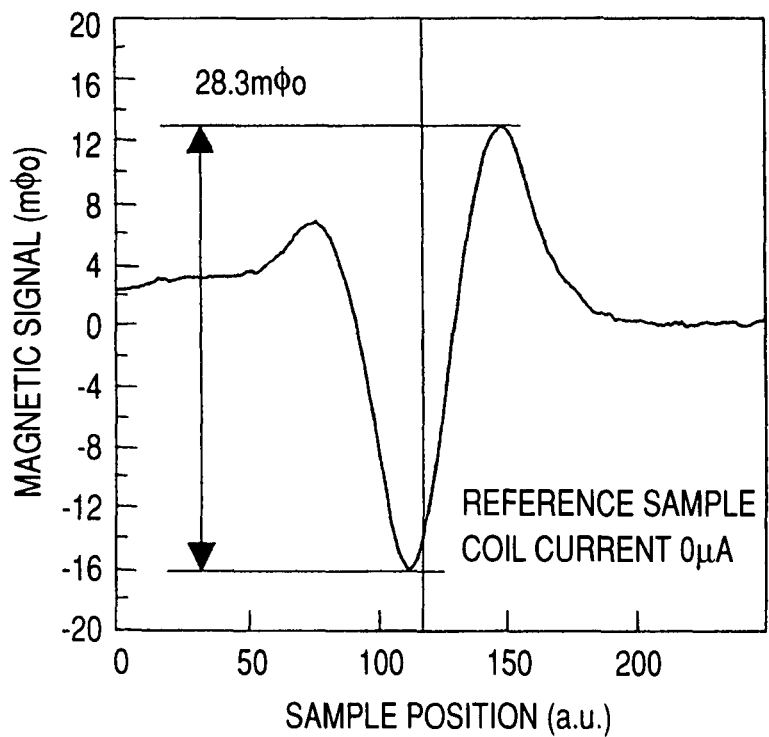
FIG. 9B is a magnetic signal waveform obtained from a reference sample not containing IgE and measured with no electrical current flowing in the compensation coil.

FIG. 9A shows the magnetic signal waveform obtained from the sample containing 100 pg of IgE; and FIG. 9B shows the magnetic signal waveform obtained from the reference sample not containing IgE. Magnetic signals were obtained from the reference sample that supposedly should not generate regular magnetic signals because of Brownian motion, showing that a magnetic field that could not be blocked by the magnetic shield remained in the vicinity of the sample measurement position. The amount of change in both waveforms was approximately the same with a difference of only 0.2 $m\phi_0$. In this data, detecting 100 pg of IgE was impossible because the variations in the reference sample was 1 $m\phi_0$ or larger.

Figure 10:
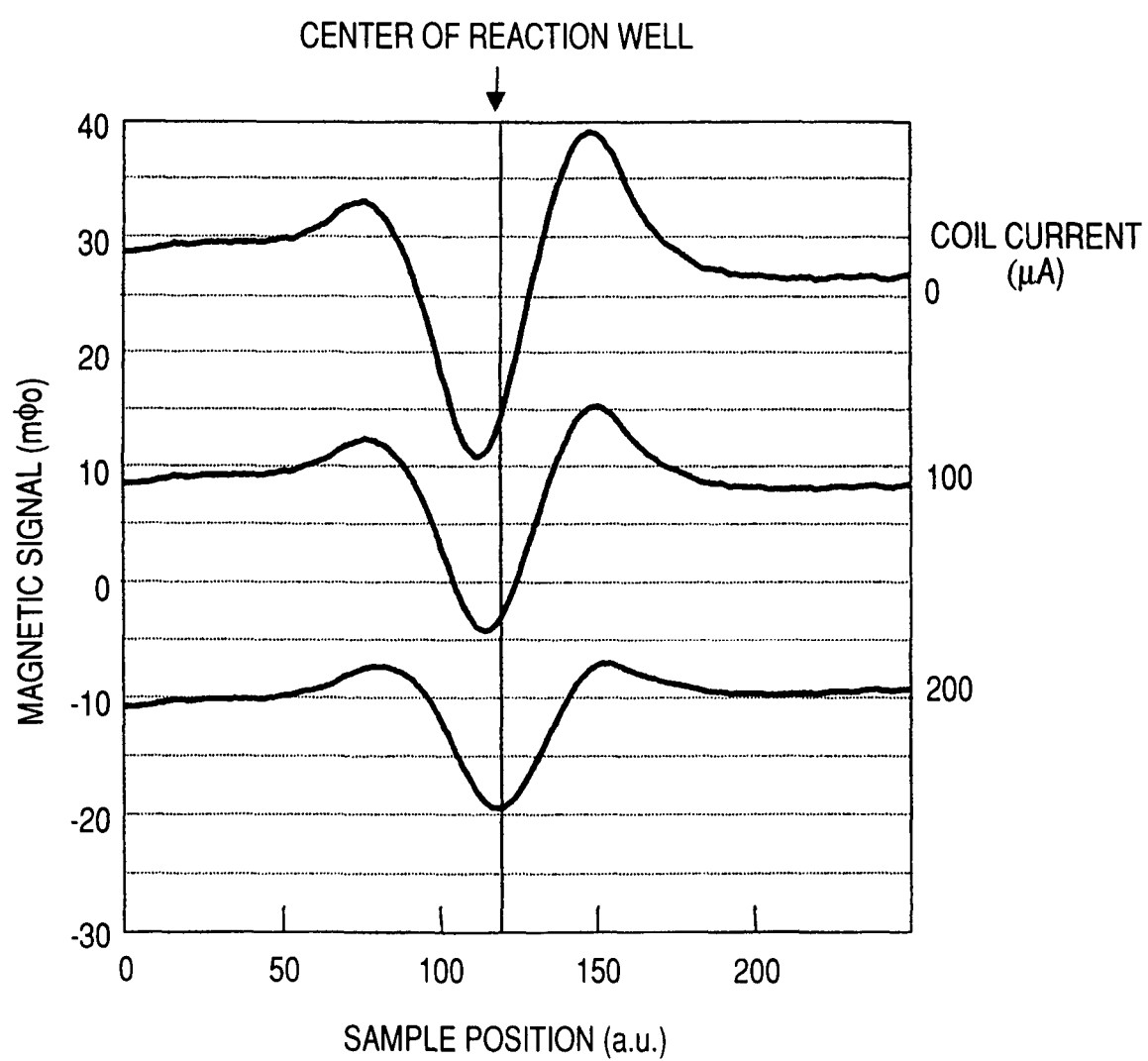
FIG. 10 is magnetic signal waveforms from the reference sample showing the compensation coil current dependence.

FIG. 10 shows the magnetic signal waveform of the reference sample when measured while an electrical current flowed in the compensation coil 16. The waveform gradually neared bilateral symmetry as the current increased in the compensation coil 16. A bilaterally symmetrical waveform was obtained when an electrical current of 200 µA flowed in the coil. When the current in the compensation coil 16 was increased still further, the offset from the bilaterally symmetrical waveform of the reference sample was inverted centering on the axis.

The magnetic signal waveform obtained when an electrical current of 200 µA flowed in the compensation coil 16 is corresponding to the waveform shown in FIG. 4A. Therefore, this result indicates that magnetic field in the z direction is canceled by the compensation coil 16. The compensation coil at this time applies a magnetic field of approximately 50 nT to the vicinity of the sample.

Figure 11A:
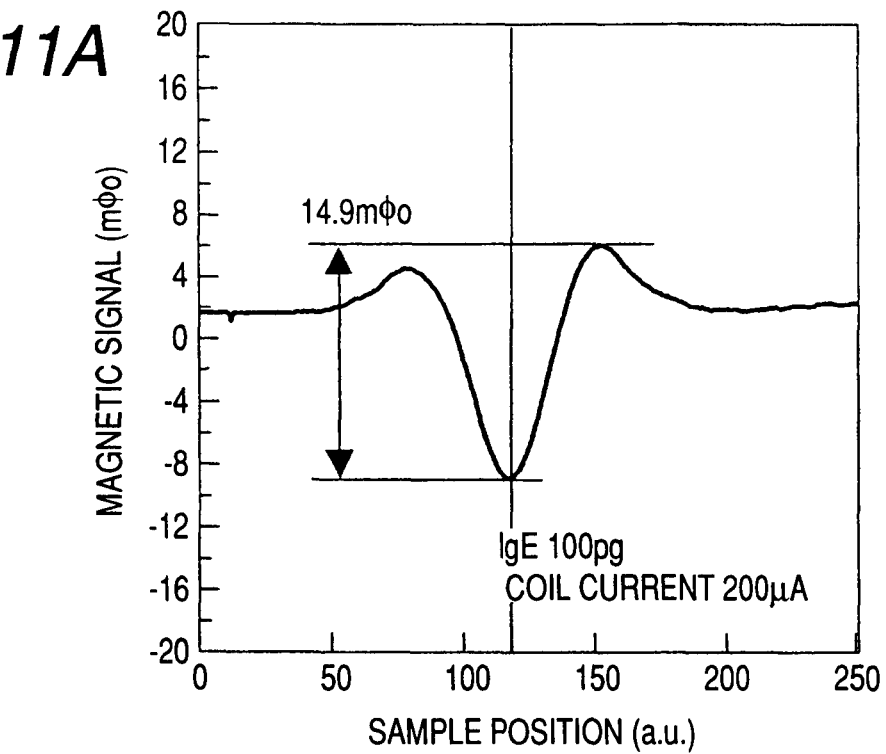
FIG. 11A is a magnetic signal waveform obtained from a sample containing 100 pg of IgE measured with an electrical current of 200 µA flowing in the compensation coil.
Figure 11B:
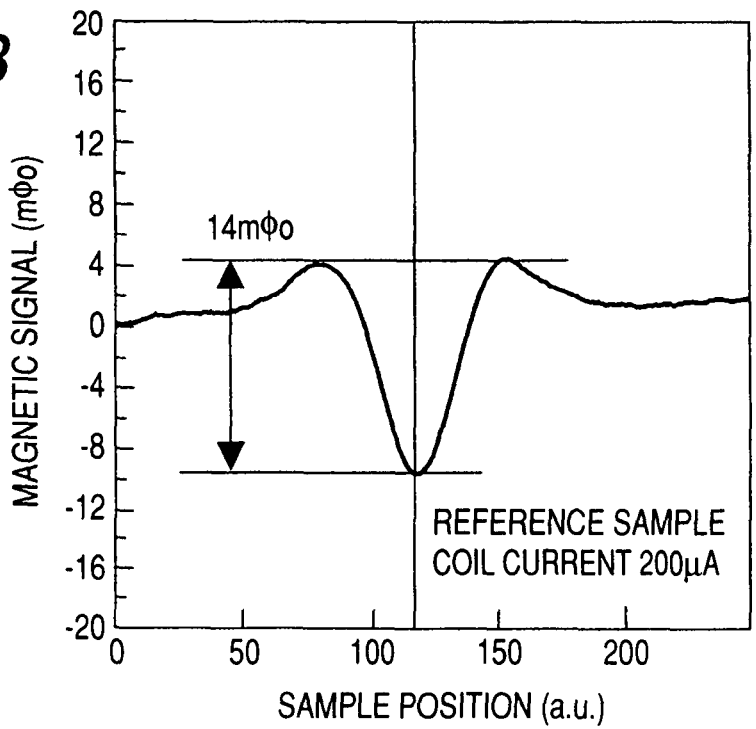
FIG. 11B is a magnetic signal waveform obtained from a reference sample not containing IgE measured with an electrical current of 200 µA flowing in the compensation coil.

FIG. 11A and FIG. 11B show magnetic signal waveforms obtained from a sample in FIG. 11A containing 100 pg of IgE measured in a state where 200 µA of electrical current is flowing in the compensation coil 16; and a sample in FIG. 11B for a reference sample not containing IgE. In this state a difference of 0.9 m$\phi_0$ was obtained. The magnetic signal waveform from the magnetic marker in the solution is bilaterally symmetrical due to the effect of the compensation coil 16 and therefore that eliminating the symmetrical signal components to extract just the nonsymmetrical components was attempted.

Figure 1A:
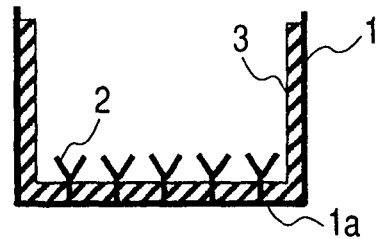
FIG. 1A through FIG. 1E are drawings showing a typical procedure for the immunoassay method of the related art.
Figure 1B:
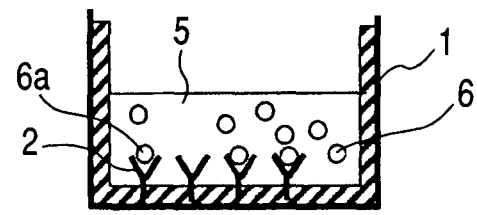
Figure 1C:
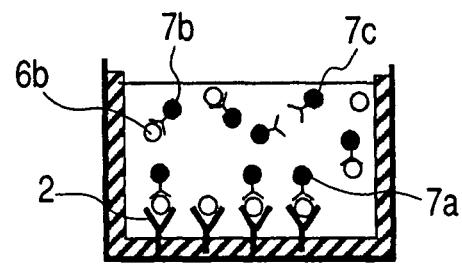
Figure 1D:
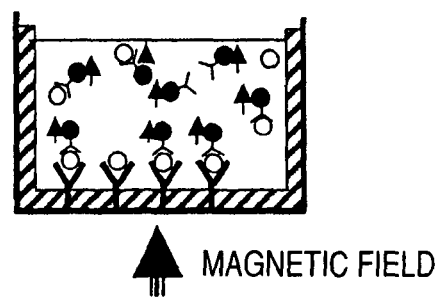
Figure 1E:
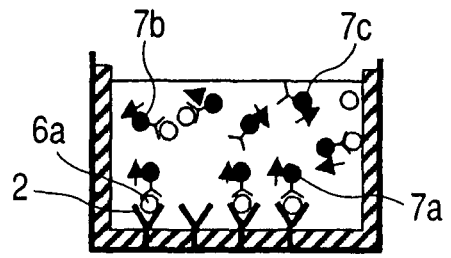
Figure 2A:
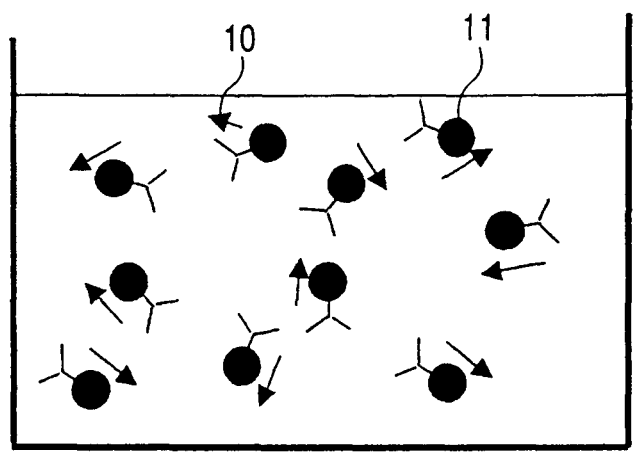
FIG. 2A and FIG. 2B are drawings showing the state of the magnetic markers when the magnetic field is completely blocked, and the magnetic marker state when there is a residual magnetic field.
Figure 2B:
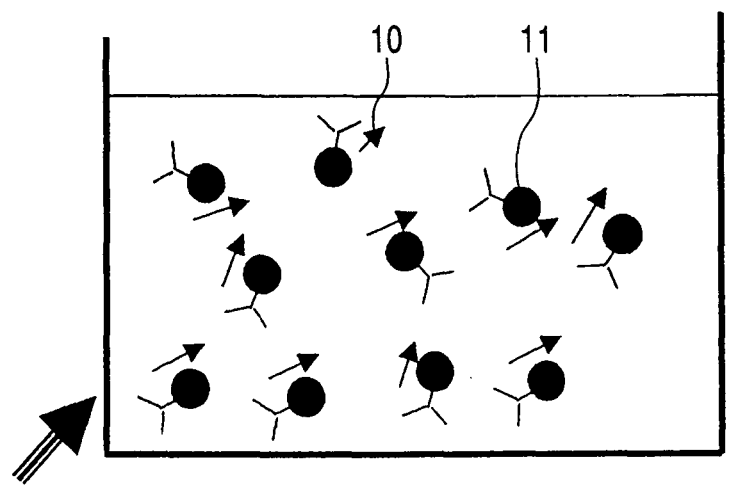
Figure 3:
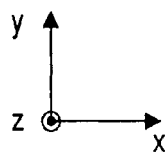
FIG. 3A, FIG. 3B and FIG. 3C are drawings showing the relation between the magnetization direction of the sample when using a magnetometer, to the detected magnetic signal waveform.
Figure 12A:
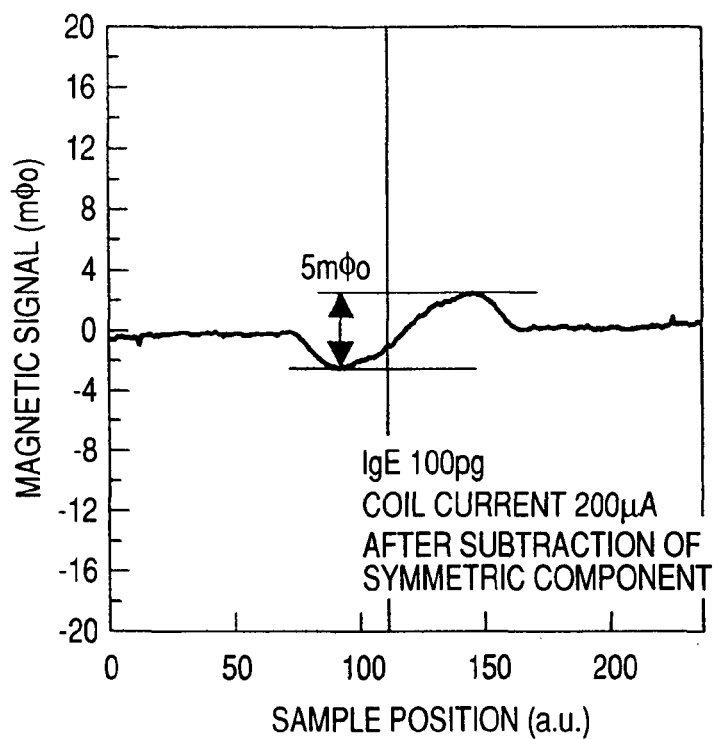
FIG. 12A is a waveform obtained from a sample where bilaterally symmetrical components were eliminated from the magnetic signal waveform measured with an electrical current of 200 µA flowing in the compensation coil.
Figure 12B:
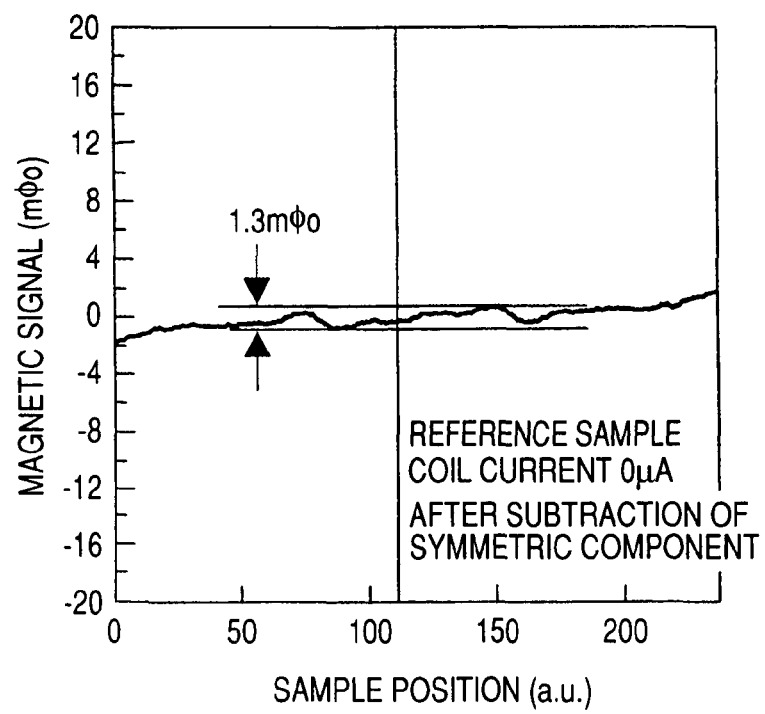
FIG. 12B is a waveform of the reference sample not containing IGE and measured with an electrical current of 200 µA flowing in the compensation coil.

FIG. 12A and FIG. 12B show waveforms where the bilaterally symmetrical components at the reaction chamber center position in the FIG. 11A and FIG. 11B waveforms were eliminated. This process can be performed by subtraction as described for FIG. 3 and FIG. 4. As can be seen in FIG. 12A, in contrast to the sharp signal with an amplitude of 5 m$\phi_0$ in the sample material containing 100 pg of IgE; the waveform in the reference sample in FIG. 12B with a maximum amplitude of 1.3 $\phi_0$ is unclear, and the effect of the unbound magnetic marker in the solution has largely been eliminated. The optimal current of the compensation coil 16 can in this way be evaluated beforehand in the first embodiment, and by allowing an appropriate amount of electrical current flow, the bound magnetic markers contained in tiny amounts in unbound magnetic markers in the liquid can be measured.

Second Embodiment

An example of the second embodiment is described utilizing a magnetic immunoassay system for detecting magnetic signals from a sample that reacted with a test reagent in a first-order planar SQUID gradiometer, using antibodies labeled with magnetic nanoparticles having remanence.

Figure 13:
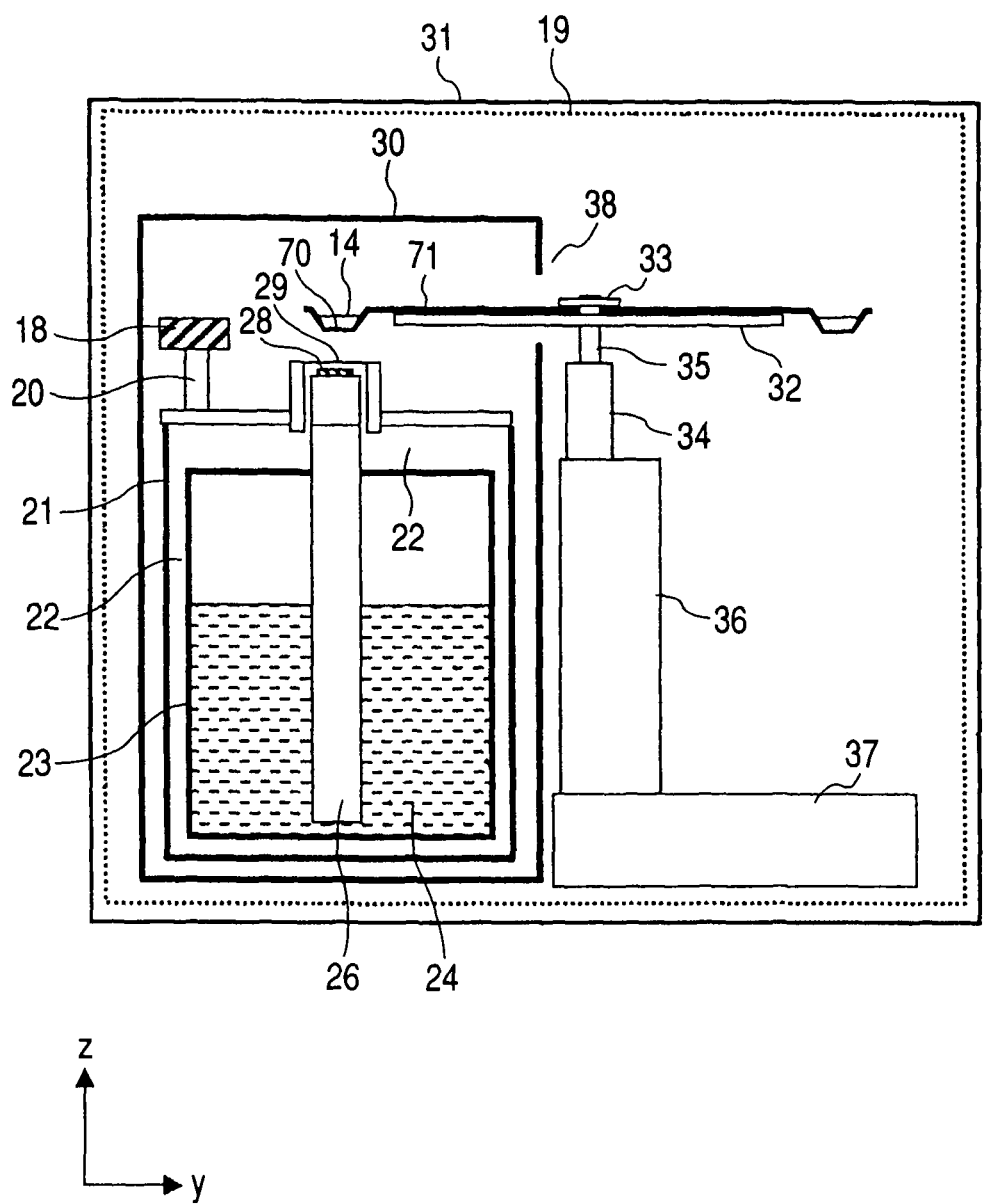
FIG. 13 is a drawing showing the structure of the immunoassay system of the second embodiment.

FIG. 13 is a cross sectional view showing the structure of the magnetic immunoassay system of the second embodiment. A permanent magnet 18 and a position adjuster 20 for the permanent magnet are installed instead of the compensation coil 16 for the system used in the first embodiment shown in FIG. 5. The permanent magnet 18 applies a magnetic field in a direction perpendicular to the magnetization direction (z direction) of the bound magnetic marker at the measurement position. The other parts of the structure are identical to the first embodiment.

A sample identical to that for the first embodiment was measured using this system. The method for making the samples was identical to that of the first embodiment. The magnetic field applied to the sample measurement position was approximately 1 nT to 100 μT. The optimal magnetic field depends on the characteristics of the magnetic marker and the strength of the residual magnetic field. Therefore just as with the first embodiment, it is important to evaluate the magnetic signal waveform produced by the permanent magnet in terms of the difference in magnetic field strength, and use a permanent magnet possessing optimal magnetic field strength. A comparatively weak rubber magnet was utilized here as the permanent magnet however an electromagnet of course may also be used.

Figure 14A:
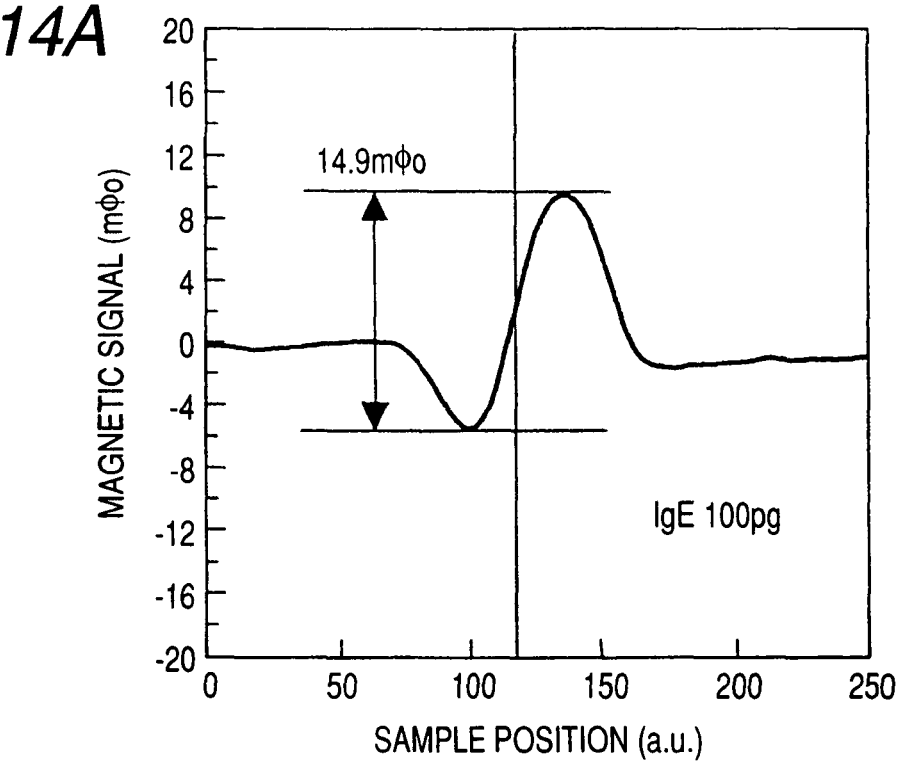
FIG. 14A is a magnetic signal waveform obtained in the second embodiment from a sample containing 100 pg of IgE.
Figure 14B:
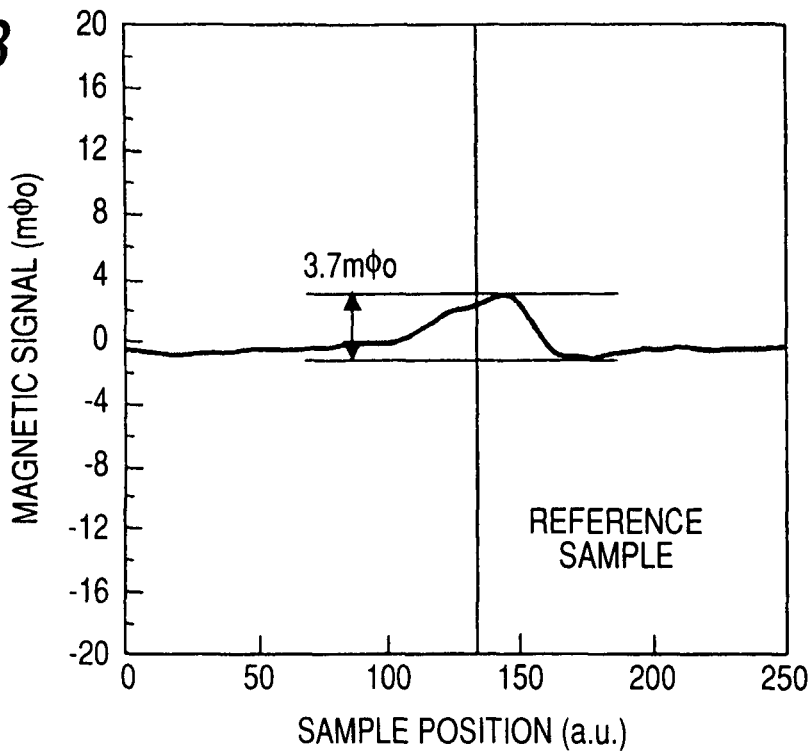
FIG. 14B is a magnetic signal waveform obtained in the second embodiment from a reference sample not containing IgE.

FIG. 14A shows a magnetic signal waveform obtained from a sample containing 100 pg of IgE. FIG. 14B shows a magnetic signal waveform obtained from a reference sample not containing IgE. The amount of change in the magnetic signal from the reference sample is one/tenth that of the waveform for the reference sample in FIG. 9B. The reason for the smaller change is that the y-direction magnetic field from the permanent magnet 18 aligns the magnetic markers in the solution in the y-direction so that the number of unbound magnetic markers aligned in the x and z directions, which are detected by SQUID, is decreased. The sample containing 100 pg of IgE can therefore be clearly distinguished from the reference sample as shown in FIG. 14A and FIG. 14B thus confirming the effect of this invention.

Third Embodiment

An example of the third embodiment is described utilizing a magnetic immunoassay system for detecting magnetic signals from a sample that reacted with a test reagent in a first-order planar SQUID gradiometer, using antibodies labeled with magnetic nanoparticles having remanence.

FIG. 15 is a cross sectional view showing the structure of the system. The system utilizes a dual layer cylindrical magnetic shield made from a cylindrical magnetic shield 43 with an inner diameter of 40 centimeters and length of 1 meter, and a cylindrical magnetic shield 44 with an inner diameter of 30 centimeters and length of 90 centimeters. The shield 43 and 44 material is 2 millimeter thick permalloy. A sample container 45 is a non-magnetic reaction chamber with an 8 by 12 array of 96 holes. The sample container 45 is supported by a sample container holder 47 so that the measurement position is at the center of the magnetic shield, and a 3-axis manipulator 48 moves the desired sample to the measurement position. A SQUID 41 utilizes a gradiometer with the structure shown in FIG. 7.

A pulse tube cryocooler 49 cools the SQUID 41 via a sapphire rod 50. The SQUID at low temperature is located within a vacuum insulation chamber 42. The temperature of the SQUID is controlled in a range of 65 to 80 K within a variation of ±0.1 K. The longitudinal direction of the gradiometer pickup coil matches the x (horizontal) direction of the sample container holder 47. Antibodies are affixed to the sample container 45. A sample 46 is a liquid sample containing unbound magnetic markers and magnetic markers bound to the target substance. After being magnetized in advance, the sample 46 is sealed into the sample container 45.

Each of the 96 hole samples were moved along the x direction to the measurement position over the SQUID by moving the entire sample container 45 and the change in magnetic signals at that time was measured. The measurement time for one row (12 samples) was from 0.1 second to several seconds. Multiple measurements were made by moving the samples back and forth over the SQUID, and the data averaging was then performed. When measurement of one row (12 samples) was completed, the entire sample container 45 was shifted along the y direction by a width equal to one row, and the same measurement made after movement to that next row.

Figure 16:
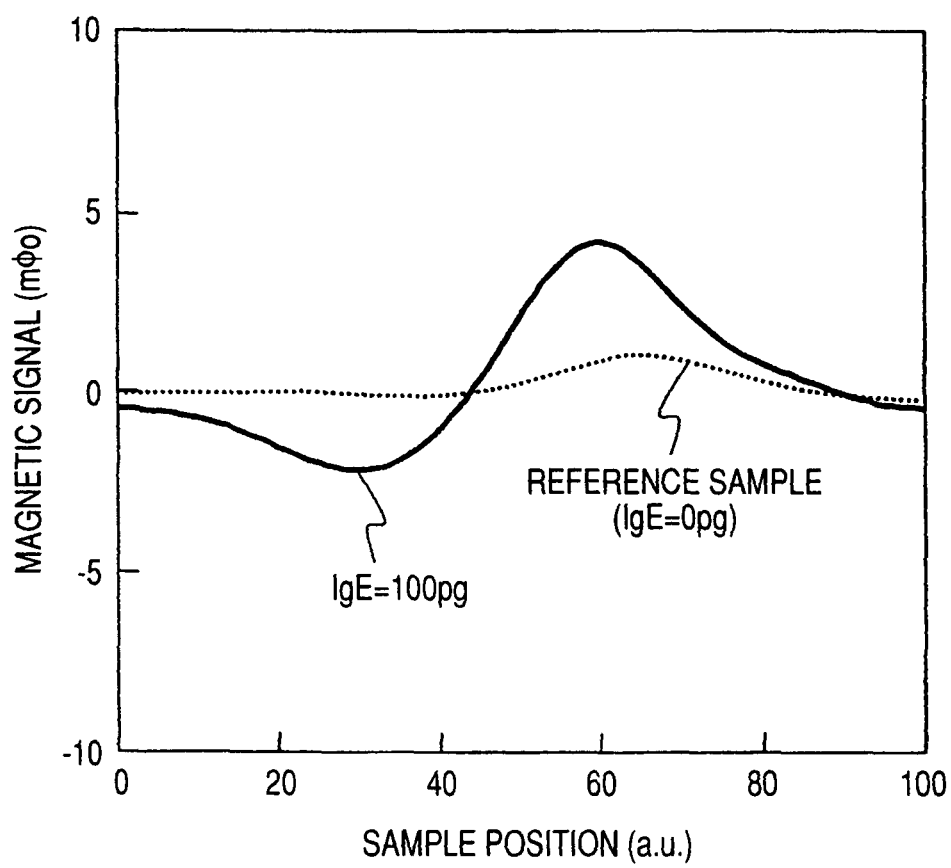
FIG. 16 is magnetic signal waveforms obtained in the third embodiment from a sample (solid line) containing 100 pg of IgE and a reference sample (dotted line) not containing IgE.

FIG. 16 shows the magnetic signal waveform (solid line) obtained from a sample containing 100 pg of IgE; and a magnetic signal waveform (dotted line) obtained from a reference sample not containing IgE. A magnetic signal fluctuation of approximately 6 m$\phi_0$ was detected in the sample containing 100 pg of IgE. A fluctuation width approximately 4 times greater than that in the reference sample was obtained. The reason is that the magnetic field remaining along the y direction within the cylindrical magnetic shield, aligned the magnetic markers in the solution along the y direction so that fewer magnetic markers along the x and z direction were detected as magnetic signals by the SQUID.

The description of the embodiments described detection of IgE as one type of antibody related to allergies. However this invention is of course not limited to IgE and may by applied to tests for substances usually measured by general immunoassay systems including for example, tests for biological substances such a hormones, cytokine, and tumor markers, as well as environmental toxins including dioxins, etc. Moreover, the examples in the embodiments were described using the sandwich method for capturing antibodies, but this invention can also be applied to the quantitative competition method and bridge method utilized in general immunoassay inspections. This invention is also effective for cases using other types of magnetic markers such as when using magnetic elements other than magnetite. The effect of this invention is also obtained when using magnetic sensors other than the high-temperature superconducting SQUID, such as when using high-sensitivity magnetic sensors including light-pumping flux meters and low-temperature superconductor (for example, Nb and $MbG_2$, etc.) SQUID, and inductive coils, flux gate flux meters, proton flux meters, MR sensors, GMR sensors, and Mi sensors, etc.

What is claimed is:

1. A magnetic immunoassay system which measures a remnant magnetic signal generated from a sample for detecting an antigen contained in the sample, comprising:
   a nonmagnetic reaction chamber where a plurality of capturing antibodies, for binding antigens to-be-detected in the sample, are affixed to a surface of the chamber;
   a mechanism which moves the reaction chamber;
   a magnetic sensor which measures the magnetic signal from the chamber containing a mixture of the sample in a liquid state antibodies which are to bind to the antigens to be detected and further which are labeled with magnetic nanoparticles;
   a magnetic shield which blocks a magnetic noise in the periphery of the magnetic sensor;
   a magnetic field compensator comprising an electromagnet and an adjustment controller for adjusting a magnetic field applied by the electromagnet, the electromagnet configured to apply a DC magnetic field relative to a sensing direction of the magnetic sensor, the DC magnetic field being in a range between 1 nano tesla and 100 micro tesla,
   the adjustment controller operatively associated with the electromagnet so as to vary current through the electromagnet to thereby direct the DC magnetic field such that the first summed magnetization direction of the first group of magnetic nanoparticles binding to the first group of the antigens that are bound to the capturing antibodies is affixed indirectly to the nonmagnetic reaction chamber square with a second summed magnetization direction of (1) a second group of magnetic nanoparticles respectively bound to a second group of the antigens that are not bound to the capturing antibodies and (2) a third group of magnetic nanoparticles that are bound to neither the first group of the antigens nor the second group of the antigens;
   a current source which supplies an optimal DC current of a predetermined value to the electromagnet; and
   a processor which processes signals from the magnetic sensor to extract signals from the first group of magnetic nanoparticles binding to the first group of the antigens that are bound to the capturing antibodies and thereby affixed indirectly to the nonmagnetic reaction chamber.

2. The magnetic immunoassay system according to claim 1, wherein the magnetic sensor is a superconducting quantum interference device.

3. The magnetic immunoassay system according to claim 1, wherein the electromagnet, which makes the first summed magnetization direction intersect the second summed magnetization direction, applies the magnetic field acting in a direction perpendicular to a pickup coil surface of the magnetic sensor for detecting magnetism.

4. The magnetic immunoassay system of claim 1, wherein the magnetic field compensator comprises a compensation coil and the adjustment controller varies current applied to the compensation coil.

5. A magnetic immunoassay system which measures a remnant magnetic signal generated from a sample, comprising:
   a nonmagnetic reaction chamber;
   nonmagnetic beads which surfaces are bound with capturing antibodies for binding to antigens to be detected;
   a mechanism which moves the reaction chamber;
   a magnetic sensor which measures the magnetic signal from the sample in a liquid state containing a first group of the antibodies labeled with a first group of magnetic nanoparticles which bind to a first group of the antigens;
   a magnetic field compensator comprising an electromagnet and an adjustment controller for adjusting a magnetic field applied by the electromagnet, the electromagnet configured to apply a DC magnetic field relative to a sensing direction of the magnetic sensor, the magnetic field being in a range between 1 nano tesla and 100 micro tesla, the adjustment controller operatively associated with the electromagnet so as to vary current through the electromagnet to thereby direct the DC magnetic field such that the first summed magnetization direction of the first group of magnetic nanoparticles binding to the first group of the antibodies which are affixed to the surfaces of the nonmagnetic beads and further bind to the first group of the antigens, the first summed magnetization direction intersecting a second summed magnetization direction of (1) a second group of magnetic nanoparticles each bound to a second group of the antigens that is not bound to the antibodies affixed to the surfaces of the nonmagnetic beads and (2) a third group of magnetic nanoparticles unbound to either the antibodies or the antigens;
   a current source which supplies an optimal DC current of a predetermined value to the electromagnet; and
   a processor which processes signals from the magnetic sensor to extract signals from the first group of magnetic nanoparticles labeling the first group of the antibodies which are affixed to the surfaces of the nonmagnetic beads and bound to the first group of the antigen.

6. The magnetic immunoassay system according to claim 5, wherein the magnetic sensor is a superconducting quantum interference device.

7. The magnetic immunoassay system according to claim 5, wherein the electromagnet, which makes the first summed magnetization direction intersect the second summed magnetization direction, applies the magnetic field acting in a direction perpendicular to a pickup coil surface of the magnetic sensor for detecting magnetism.

8. The magnetic immunoassay system of claim 5, wherein the magnetic field compensator comprises a compensation coil and the adjustment controller varies current applied to the compensation coil.

* * * * *